United States Patent [19]
Engelbrecht et al.

[11] Patent Number: 6,120,294
[45] Date of Patent: Sep. 19, 2000

[54] TWO COMPONENT KIT AND PIN BASED ON GUTTA-PERCHA FOR USE WITH THE KIT

[75] Inventors: Jürgen Engelbrecht, Hamburg; Jürgen Eberlein; Werner Mannschedel, both of Langenau; Wolfram Ziegler, Bokholt-Henredder, all of Germany

[73] Assignee: ROEKO GmbH & Co Dentalerzeugnisse, Langenau, Germany

[21] Appl. No.: 09/037,637

[22] Filed: Mar. 10, 1998

[30] Foreign Application Priority Data

Mar. 10, 1997 [DE] Germany .............................. 197 09 531

[51] Int. Cl.$^7$ ........................................................ A61C 5/00
[52] U.S. Cl. ........................... 433/228.1; 523/116; 106/35
[58] Field of Search ....................................... 433/102, 224, 433/228.1, 81; 523/116; 106/35

[56] References Cited

U.S. PATENT DOCUMENTS

| 4,449,938 | 5/1984 | Pollak | 433/228.1 X |
| 5,106,301 | 4/1992 | Wiyahara et al. | 433/224 X |

*Primary Examiner*—Nicholas D. Lucchesi
*Attorney, Agent, or Firm*—Pitney, Hardin, Kipp & Szuch, LLP

[57] ABSTRACT

The invention relates to a kit having two components which harden upon mixing and are suitable for a root-filling material. Further, the invention relates to a pin on the basis of gutta-percha as an optional further component of the kit.

14 Claims, No Drawings

TWO COMPONENT KIT AND PIN BASED ON GUTTA-PERCHA FOR USE WITH THE KIT

The invention relates to a kit with two components, which harden upon mixing and are suited for filling a root canal. The invention further relates to a pin based on gutta-percha as an optimal further component for the kit.

The European Patent EP-BL 0 563 749 discloses an X-ray-opaque material consisting of two phases for preparing provisional crowns and bridges, where the phases comprise a paste formed of difunctional acrylates, activators and X-ray-opaque fillers, and non-polymerisable (inert) softeners, catalysts and structural agents.

These known materials are not intended as a material for filling roots.

The German Patent Application DE-A1 3 915 592 discloses a dental cement comprising a hardening fluid, namely a silicone oil modified with carboxyl groups, and a hardening accelerator, namely a metal oxide and/or metal hydroxide.

This known dental cement hardens to a cement-like mass which includes inorganic salts of the acidic silicone oil. The removal of the hardened dental cement from the root canal is however problematic and can lead to undesired damage of the root canal. Withdrawing the dental cement in one piece from the canal is not possible.

The U.S. Pat. No. 3,082,526 discloses a mixture for filling root canals which comprises a diorganosiloxane with end hydroxl groups of the formula $HO(R_2SiO)_nH$, and an organotriacryloxisilane of the formula $RSi(OAc)_3$.

The two components undergo cross-linking in a condensation reaction, which however can lead to undesired shrinkage due to the separation of HOAc.

As disclosed in U.S. Pat. No. 3 127 363, the following two components undergo a cross-linking condensation:

an organosiloxane (A) of the general formula $XO—Si(R)_2—[O—SiR_2]_n—O—Si(R)_2—OX$, and a trifunctional cross-linking agent (B) for example of the formula $RSi(OH)_3$.

According to this patent (col. 8, line 43), the known composition can be used for closing side gaps or spaces formed between a root canal and a pin inserted into the canal. As this prior art makes use of a condensation reaction, the above-mentioned undesired shrinkage cannot be excluded.

The document DE 37 43 983 relates to an X-ray contrast and moulding material for monitoring the root canal. The silicone moulding mass includes hydroxydimethylpolysiloxanes with hydroxide groups on either end and ortho- or polyehtylsilicates with an ethoxy group as cross-linking agent or vinylpolymethylsiloxanes with a vinyl group at the end, hydrogen polymethylsiloxane with an active hydrogen on both ends and catalysts for addition polymerisation, such as catalysts on the basis of platinum. Such compositions, however react by separating condensation products, which lead to the above-mentioned disadvantages, or they lead to dimeric compounds due to the mono-functional vinyl polymethylsiloxanes with a single vinyl group, which are not cross-linked and can be easily decomposed. These products are not sufficiently stable for permanent placement in a tooth. In particular, a monomer residue remains in the filling which can be carried off with tissue fluid, etc. This produces lesions in the root canal filling and can lead to bacteria pobulations which can cause an infection. Moreover this can lead to long-term release of physiologically undesirable monomers.

The object of the present invention is to provide a root-filling material, which can be easily applied to an opened root canal, closes the canal well, also closes side gaps or spaces formed by the root canal and one or more inserted pins, closes spaces formed between the pins and which can be removed as one piece as far as possible without damaging the root canal.

A further object of the invention is to provide a root-filling material capable of remaining in the tooth over a long time period, for example 10 to 15 years, without the occurrence of holes or physiologically questionable substances being released.

According to an embodiment of the invention, a kit is provided with two components, which hardens upon mixing with one another to form a suitable root-filling material, wherein one of the two components (Component I) consists of or includes one or more silicone oils, which comprises at least two SiH groups, the other of the two components (Component II) consists of or includes one or more silicone oils, which comprises at least two vinyl groups, and one of the two components additionally includes a catalyst for an addition reaction or an addition cross-linking of the two components I and II.

With the kit according to the invention, it has been shown that root canal fillings can be prepared, which are easy to apply, offer an excellent sealing of aide gaps as well as sealing between optionally employed pins and which can be easily removed as a whole piece when necessary. In particular, the components according to the invention are cross-linked in three dimensions, whereby no monomers remain. Such materials are stable over long time periods, i.e. they can remain in the root canal without problem for 10 or even 15 years, without lesions in the filling and without the release of monomers, etc. In addition, the filling material according to the invention is stable with respect to form.

To prepare the materials, cross-linking mixtures of vinyl silicones and hydrogen silicones in highly fluid conditions are employed according to the invention. Regarding the viscosity of the components of the kit and their mixtures, the skilled person can refer by way of example to EP-B1 0 563 749. Examples for self-mixing systems are further disclosed in EP-A1 0 232 733 and EP-A1 0 261 466. These mixing systems are well suited for addition cross-linking systems (in contrast to condensation cross-linking systems). Adding the completely mixed system can be greatly simplified with a fine and piece located at the end of the static mixer.

The kit according to a preferred embodiment of the invention is characterised in that the at least one silicone oil with vinyl groups comprises at least three vinyl groups and/or the at least one silicone oil with SiH groups comprises at least three SiH groups. By suitable selection of the respective number of functional groups, the properties of the materials can be adjusted, for example, cross-linking, hardness, elasticity, etc.

According to the invention, the silicone oil with vinyl groups can also contain small amounts of monofunctional silicone oils, particularly vinyl polymethyldisiloxane. The content of the silicone oils with only one vinyl group however should not exceed 5 wt.-% based on the total amount of silicone oils with vinyl groups. Preferably, the amount should not exceed 2 wt.-%, while most preferably the components contain absolutely no silicone oil with only one vinyl group.

Examples of silicone oils with at least two vinyl groups include divinylpolymethyldisiloxanes and/or trivinylpolymethylsiloxanes.

According to the invention, the silicone oil with SiH groups can also contain small amounts of monofunctional silicone oils. The content of silicone oils with only one SiH group should however not exceed 5 wt.-% based on the total amount of silicone oils with SiH groups. Preferably, the amount should not exceed 2 wt.-%, while it is most preferred that the components contain no silicone oil with only one SiH group Examples of the silicone oil according to the present invention having at least two SiH groups include hydrogen polymethyldisiloxanes.

A compound containing platinum can be used as the catalyst, for example hexachloroplatinic acid.

The components I and II of the kit according to the invention can also comprise the usual additives, in particular inert fillers, especially inert inorganic fillers such as quartz or aluminium oxide at least one X-ray contrast agent, selected from the group of zinc, ytterbium, yttrium, gadolinium, zirconium, strontium, wolfram, tantalum, niobium, barium, bismuth, molybdenum and lanthanum powder, powdered alloys thereof, oxides, fluorides, sulfates, carbonates, wolframates and carbides thereof, ion-donating fillers, thixotropic fillers, preferably silicic acid, plastifying additives, preferably, silicone oil and/or paraffin oil, and/or disinfecting and/or devitalizing additives.

The X-ray contrast agent according to the invention can have a grain size of 0.1 to 50 micrometer, preferably 0.3 to 40 micrometer, more preferably 0.5 to 30 micrometer, even more preferred 0.8 to 20 micrometer, and most preferred 1 to 10 micrometer. If the grain is too large, the material is too coarse and could possibly not be readily applied to the root canal. If the grain is too fine, its surface area is too large which also leads to problems.

The ion-donor filler according to the invention can be calcium, zinc, carbonate, fluoride, and/or phosphate-containing agents. Examples of calcium-containing additives include calcium carbonate, hydroxlapatite, tricalciumphosphate and tetracalciumphosphate. Zinc oxide can be used as the zinc-containing additive. Glasses can also be used as the ion-donor filler.

Regarding the thixotropic fillers, amorphous silicone dioxide modifications can be mentioned, for example, pyrogenic and precipitated silicic acid as well as diatomaceous earth. Particularly suited.,are agglomerated pyrogenic silicic acids or sintered silica gel, as described for example in EP-0 040 232 and EP-0 113 926. These fillers have little tendency to thicken and have the property that their thixotropic behaviour is uniform and hardly dependent upon how fast the processing takes place.

According to the invention, it is expedient to provide the two components I and II of the kit in the relationship 10:90 to 90:10, preferably in the relationship 40:60 to 60:40 and most preferred in substantially equal amounts based on volume.

Such a relationship is particularly advantageous when one works with the self-mixing systems according to EP-0 232 733 or EP-0 261 466. The components of the kit according to the invention can also be provided in separate cartridges.

According to a further embodiment of the invention, one or more pins of isoprene base are provided as an optional further component of the kit, particularly on the basis of transpolyisoprene, gutta-percha or balata. The pin can be impregnated with a silicone oil of the present invention comprising SiH groups.

For such a pin, one can start with a primary solution containing the hydrogenated silicone, which chemically reacts with an unsaturated group of the pin and forms a solid bond. For the silicone oil with SiH group, one can again use the hydrogen polymethyldisiloxane.

When an impregnated pin or several such pins according to the invention are inserted into an opened root canal and the intermediate gaps are filled with the aid of the kit according to the invention, the pin bonds with the hardened root filling material such that the pin can easily be removed later as a whole together with the kit.

Naturally it is also possible to provide a pin which is impregnated with a silicone oil with SiH groups according to the invention in a mixture with at least one silicone oil according to the invention with vinyl groups. This at least one silicone oil with vinyl groups should at maximum have only a small amount of monofunctional silicone oil, for example vinyl polymethyldisiloxane, in combination with a main amount of a polyfunctional silicone oil, in particular a bi-functional silicone oil such as divinylpolymethyldisiloxane or a polyfunctional silicone oil.

In the following, the invention is discussed in more detail in conjunction with the examples.

EXAMPLE 1

Preparation of a Root-filling Material on the Basis of Addition Cross-linking Silicones One prepares a mixture A from the following ingredients:

| | |
|---|---|
| Trivinylpolymethyldisiloxane | 66 Parts |
| Vinylpolymethyldisiloxane | 2 Parts |
| Hydrogen polymethyldisiloxane with 2 SiH groups | 15 Parts |
| Paraffin oil | 12 Parts |
| Pyrogenic silicic acid | 5 Parts |
| Evacuation is performed after complete mixing. In addition, a mixture B is prepared with the following ingredients | |
| Trivinylpolymethyldisiloxane | 68 Parts |
| Silicone oil | 27 Parts |
| Hexachloroplatinic acid (catalyst) | 0.0001 Part |
| Pyrogenic silicic acid | 5 Parts |

Evacuation is also performed after complete mixing.

Mixture A and mixture B are added in equal parts to a dual cartridge with a static mixer and directly applied in a prepared root canal or one dips a gutta-percha applicator in this mixture and applies it to the root canal in this manner. Within 10 minutes, the entire mixture is hardened. The silicone filler according to the invention closes the canal free of gaps.

EXAMPLE 2

Preparation and Use of a Primer for Gutta-Percha Pins

One prepares a solution of the following ingredients:

| | |
|---|---|
| Hydrogen polymethyldisiloxane (primer) with 2 SiH Groups | 10 Parts |
| Toluene | 90 Parts |

The solution is applied to a gutta-percha pin and dried. After applying the combined mixture of mixture A and B of example 1 in a prepared root canal, the gutta-percha pin is inserted in the root canal. After hardening of the root canal filler mass according to the invention, the gutta-percha pin is fully bonded with the mass The gutta-percha pin together with the entire root-filling material can be easily removed from the root canal.

What is claimed is:

1. A mixture suitable for use as a root-filling material comprising:
    a first component comprising at least one silicone oil having at least two SiH groups;
    a second component comprising at least one silicone oil having at least two vinyl groups; and
    a catalyst which causes the cross-linking of the first component and the second component and causes the two components to harden when mixed together.

2. The mixture according to claim 1, wherein the at least one silicone oil with vinyl groups includes at least three vinyl groups.

3. The mixture according to claim 1, wherein the at least one silicone oil with SiH groups includes at least three SiH groups.

4. The mixture according to claim 1, further comprising a mixture of up to 5 wt.-% monofunctional and at least 95 wt.-% poly-functional silicone oils with vinyl groups.

5. The mixture according to claim 1, further comprising a mixture of up to 5 wt.-% monofunctional and at least 95 wt.-% polyfunctional silicone oils with SiH groups.

6. The mixture according to claim 1, wherein the silicone oil with SiH groups comprises hydrogen polymethyldisiloxane.

7. The mixture according to claim 1, the catalyst, hexachloroplatinic acid.

8. The mixture according to claim 1, further comprising at least one of the following additives:
    inert inorganic fillers;
    at least one X-ray contrast agent selected from the group of zinc, ytterbium, yttrium, gadolinium, zirconium, strontium, wolfram, tantalum, niobium, barium, bismuth, molybdenum and lanthanum powder, powdered alloys thereof, oxides, fluorides, sulfates, carbonates, wolframates, and carbides thereof;
    glasionomer powder;
    plastifying agents;
    thixotropic fillers;
    ion-donor fillers;
    at least one of disinfecting agents and devitalizing agents.

9. The mixture according to claim 8, further comprising an inorganic carrier comprising at least one of calcium, zinc, carbonate, fluoride and phosphate containing agents.

10. The mixture according to claim 1, wherein each of the components is provided in substantially equal amounts on a volume basis.

11. The mixture according to claim 1, wherein each of the components is provided in a separate cartridge.

12. The mixture according to claim 11, wherein the cartridges are insertable in a static mixing application device.

13. The mixture according to claim 1, further comprising a pin of isoprene-base, wherein the pin is impregnated with at least one silicone oil having SiH groups.

14. The mixture according to claim 13, the pin is impregnated with at least one silicone oil having SiH groups mixed with a least one silicone oil having vinyl groups.

* * * * *